(12) United States Patent
Brun et al.

(10) Patent No.: US 9,952,168 B2
(45) Date of Patent: Apr. 24, 2018

(54) IMPEDANCE MEASURING DEVICE FOR BIOLOGICAL SAMPLES AND IMPEDANCE MEASURING SYSTEM FOR BIOLOGICAL SAMPLES

(71) Applicant: Sony Corporation, Tokyo (JP)

(72) Inventors: Marcaurele Brun, Tokyo (JP); Kazumasa Sato, Tokyo (JP)

(73) Assignee: Sony Corporation, Tokyo (JP)

( * ) Notice: Subject to any disclaimer, the term of this patent is extended or adjusted under 35 U.S.C. 154(b) by 0 days.

(21) Appl. No.: 14/761,667

(22) PCT Filed: Dec. 26, 2013

(86) PCT No.: PCT/JP2013/084887
§ 371 (c)(1),
(2) Date: Jul. 17, 2015

(87) PCT Pub. No.: WO2014/115478
PCT Pub. Date: Jul. 31, 2014

(65) Prior Publication Data
US 2015/0323480 A1    Nov. 12, 2015

(30) Foreign Application Priority Data
Jan. 28, 2013    (JP) ................................ 2013-013134

(51) Int. Cl.
*G01N 9/30* (2006.01)
*G01N 33/00* (2006.01)
(Continued)

(52) U.S. Cl.
CPC ........... *G01N 27/021* (2013.01); *G01N 33/49* (2013.01); *G01N 33/4905* (2013.01); *G01N 27/02* (2013.01)

(58) Field of Classification Search
CPC .......... G01N 9/30; G01N 33/00; G01N 27/00; G01N 33/86
(Continued)

(56) References Cited

U.S. PATENT DOCUMENTS 7,537,571 B2 * 5/2009 Freeman et al. .............. 600/583
8,132,446 B2  3/2012 Hayashi
(Continued)

FOREIGN PATENT DOCUMENTS

JP      05-060749 A     3/1993
JP   2003-526108 A     9/2003
(Continued)

OTHER PUBLICATIONS

U.S. Appl. No. 12/472,630, filed May 27, 2009, Hayashi.
(Continued)

*Primary Examiner* — Brian J. Sines
(74) *Attorney, Agent, or Firm* — Wolf, Greenfield & Sacks, P.C.

(57) ABSTRACT

Provided is an impedance measuring device for biological samples including one or a plurality of biological sample holding units configured to hold a biological sample, an applying unit configured to apply an AC voltage to a pair of electrodes in contact with the biological sample held by the biological sample holding unit, a measuring unit configured to measure an impedance of the biological sample obtained by an AC voltage being applied to the biological sample by the applying unit, and a measurement condition control unit configured to control a measuring time and/or a measuring frequency in the measuring unit.

16 Claims, 7 Drawing Sheets

(51) Int. Cl.
*G01N 27/00* (2006.01)
*G01N 33/86* (2006.01)
*G01N 27/02* (2006.01)
*G01N 33/49* (2006.01)

(58) Field of Classification Search
USPC ...... 422/50, 68.1, 63, 72, 73, 82.01; 436/69, 436/66, 43, 149
See application file for complete search history.

(56) References Cited

U.S. PATENT DOCUMENTS

| | | | |
|---|---|---|---|
| 8,158,374 B1* | 4/2012 | He et al. | 435/7.92 |
| 8,357,274 B2* | 1/2013 | Marquant et al. | 204/403.01 |
| 8,372,016 B2* | 2/2013 | Freeman et al. | 600/583 |
| 8,478,546 B2 | 7/2013 | Katsumoto et al. | |
| 9,097,635 B2 | 8/2015 | Hayashi | |
| 2001/0045355 A1 | 11/2001 | Gephart et al. | |
| 2006/0160164 A1 | 7/2006 | Miller et al. | |
| 2009/0293595 A1 | 12/2009 | Hayashi | |
| 2010/0136606 A1 | 6/2010 | Katsumoto et al. | |
| 2012/0035450 A1 | 2/2012 | Hayashi | |
| 2012/0137753 A1 | 6/2012 | Hayashi | |
| 2012/0238026 A1* | 9/2012 | Hayashi et al. | 436/69 |
| 2015/0377763 A1 | 12/2015 | Brun et al. | |
| 2016/0011170 A1 | 1/2016 | Brun et al. | |
| 2016/0018346 A1 | 1/2016 | Hayashi et al. | |
| 2016/0025610 A1 | 1/2016 | Katsumoto et al. | |
| 2016/0282366 A1 | 9/2016 | Hayashi et al. | |
| 2016/0299124 A1 | 10/2016 | Brun et al. | |

FOREIGN PATENT DOCUMENTS

| | | |
|---|---|---|
| JP | 2009-042141 A | 2/2009 |
| JP | 2010-181400 A | 8/2010 |
| JP | 2011-013005 A | 1/2011 |
| JP | 2011-039070 A | 2/2011 |
| JP | 2011-112497 A | 6/2011 |

OTHER PUBLICATIONS

U.S. Appl. No. 12/733,031, filed Feb. 3, 2010, Katsumoto et al.
U.S. Appl. No. 13/371,881, filed Feb. 13, 2012, Hayashi.
U.S. Appl. No. 14/763,980, filed Jul. 28, 2015, Brun et al.
U.S. Appl. No. 14/772,483, filed Sep. 3, 2015, Brun et al.
U.S. Appl. No. 14/772,550, filed Sep. 3, 2015, Hayashi et al.
U.S. Appl. No. 14/775,099, filed Sep. 11, 2015, Katsumoto et al.
U.S. Appl. No. 14/777,906, filed Sep. 17, 2015, Brun et al.
U.S. Appl. No. 14/778,277, filed Sep. 18, 2015, Hayashi et al.
Raicu et al., Hemagglutination (Rouleau formation) judging from dielectric behavior of the whole blood [Zenketsu no Yuden Kyodo kara Mita Sekkekkyu Gyoshu (Renzen Keisei)], Journal of the Society for Bioscience and Bioengineering, Japan. 2000; 78(5): 162-65.

* cited by examiner

IMPEDANCE MEASURING DEVICE FOR BIOLOGICAL SAMPLES AND IMPEDANCE MEASURING SYSTEM FOR BIOLOGICAL SAMPLES

CROSS REFERENCE TO RELATED APPLICATIONS

This application is a U.S. National Stage Application under 35 U.S.C. § 371, based on International Application No. PCT/JP2013/084887, filed Dec. 26, 2013, which claims priority to Japanese Patent Applications JP 2013-013134, filed Jan. 28, 2013, each of which is hereby incorporated by reference in its entirety.

TECHNICAL FIELD

The present technology relates to an impedance measuring device for biological samples. More specifically, the present technology relates to an impedance measuring device for biological samples and an impedance measuring system for biological samples capable of automatically performing the impedance measurement of a biological sample.

BACKGROUND ART

There are cases where the electrical characteristics of a biological sample are measured and the measurement results are used to determine the properties of the sample or to discriminate the types of cells etc. contained in the sample (e.g. see Patent Literature 1). As the electrical characteristics to be measured, complex dielectric constant and its frequency dispersion (dielectric spectrum) are given. The complex dielectric constant and its frequency dispersion are generally calculated by using a solution holder or the like including electrodes for applying a voltage to a solution and measuring the complex capacitance or the complex impedance between the electrodes.

Furthermore, for example, Patent Literature 2 discloses a technology in which information on blood coagulation is acquired from the dielectric constant of blood, and describes "a blood coagulation system analyzing device including a pair of electrodes, applying means for applying an AC voltage to the pair of electrodes at prescribed time intervals, measuring means for measuring the dielectric constant of blood disposed between the pair of electrodes, and analyzing means for analyzing the degree of working of a blood coagulation system using the dielectric constant of blood measured at the time intervals after the anticoagulant effect working on the blood is removed."

Furthermore, for example, Patent Literature 3 discloses a blood cell analyzing device capable of evaluating effects and side effects of a drug in a short time by including a measuring unit that measures the complex dielectric constant spectrum of a suspension containing one or a plurality of blood cells, a detection unit that calculates the dielectric variable and/or the electrical property value of the suspension on the basis of the complex dielectric constant spectrum measured in the measuring unit and uses the calculated value to detect a condition change of the blood cell accompanying drug administration.

CITATION LIST

Patent Literature

Patent Literature 1: JP 2009-042141A
Patent Literature 2: JP 2010-181400A
Patent Literature 3: JP 2011-112497A

SUMMARY OF INVENTION

Technical Problem

As described above, there are cases where the impedance of a biological sample is measured to obtain various pieces of information on the biological sample or to analyze the condition of the biological sample. To enhance measurement precision, it is very important to finely set the measurement conditions etc. of the impedance in accordance with the type, analysis objective, etc. of the biological sample.

However, in conventional devices, there have been cases where it is necessary to set the measurement conditions each time in accordance with the type, analysis objective, etc. of the biological sample and the condition setting takes a long time in order to enhance measurement precision.

Thus, a main object of the present technology is to provide, in the impedance measurement of a biological sample, a measuring device capable of improving measurement precision rapidly in accordance with the type, analysis objective, etc. of the biological sample.

Solution to Problem

That is, according to the present technology, first, there is provided an impedance measuring device for biological samples including one or a plurality of biological sample holding units configured to hold a biological sample, an applying unit configured to apply an AC voltage to a pair of electrodes in contact with the biological sample held by the biological sample holding unit, a measuring unit configured to measure an impedance of the biological sample obtained by an AC voltage being applied to the biological sample by the applying unit, and a measurement condition control unit configured to control a measuring time and/or a measuring frequency in the measuring unit.

In control of the measuring time in the measurement condition control unit, a measuring interval in the measuring unit may be controlled.

In control of the measuring time in the measurement condition control unit, a timing of measurement completion in the measuring unit may be controlled.

The impedance measuring device for biological samples according to the present technology may include a temperature control unit configured to control a temperature in the biological sample holding unit.

In the biological sample holding unit, a biological sample may be held by holding a container in which the biological sample is stored.

The impedance measuring device for biological samples according to the present technology may include a biological sample supplying unit configured to supply the biological sample to the biological sample holding unit automatically.

The impedance measuring device for biological samples according to the present technology may include a drug supplying unit configured to supply one or more kinds of drug to the biological sample holding unit automatically.

One or more kinds of drug may be stored in the container beforehand.

An example of the biological sample that can be measured by the impedance measuring device according to the present technology is the biological sample containing a blood component.

The impedance measuring device for biological samples according to the present technology may include a blood condition analyzing unit configured to analyze a condition change of blood from a temporal change of an impedance measured in the measuring unit.

The impedance measuring device for biological samples according to the present technology may include a precision managing unit configured to perform management of precision of the measuring unit.

The impedance measuring device for biological samples according to the present technology may further include a driving mechanism configured to move the biological sample holding unit.

In this case, the driving mechanism may move the biological sample holding unit in a direction that changes a direction of gravity applied to the biological sample held by the biological sample holding unit.

In addition, the impedance measuring device for biological samples according to the present technology may include a stirring mechanism configured to perform stirring in the biological sample holding unit.

Next, according to the present technology, there is provided an impedance measuring system for biological samples including one or a plurality of biological sample holding units configured to hold a biological sample, an applying unit configured to apply an AC voltage to a pair of electrodes in contact with the biological sample held by the biological sample holding unit, a measuring unit configured to measure an impedance of the biological sample obtained by an AC voltage being applied to the biological sample by the applying unit, a measurement condition control unit configured to control a measuring time and/or a measuring frequency in the measuring unit, a display unit configured to display data of an impedance measured in the measuring unit, and a user interface for a user's operation.

The impedance measuring system for biological samples according to the present technology may include a memory unit configured to store data of an impedance measured in the measuring unit.

Advantageous Effects of Invention

An impedance measuring device for biological samples according to the present technology can automatically control the measuring time and/or the measuring frequency, and can therefore, in the impedance measurement of a biological sample, improve measurement precision rapidly in accordance with the type, analysis objective, etc. of the biological sample.

DESCRIPTION OF EMBODIMENTS

Figure 1:
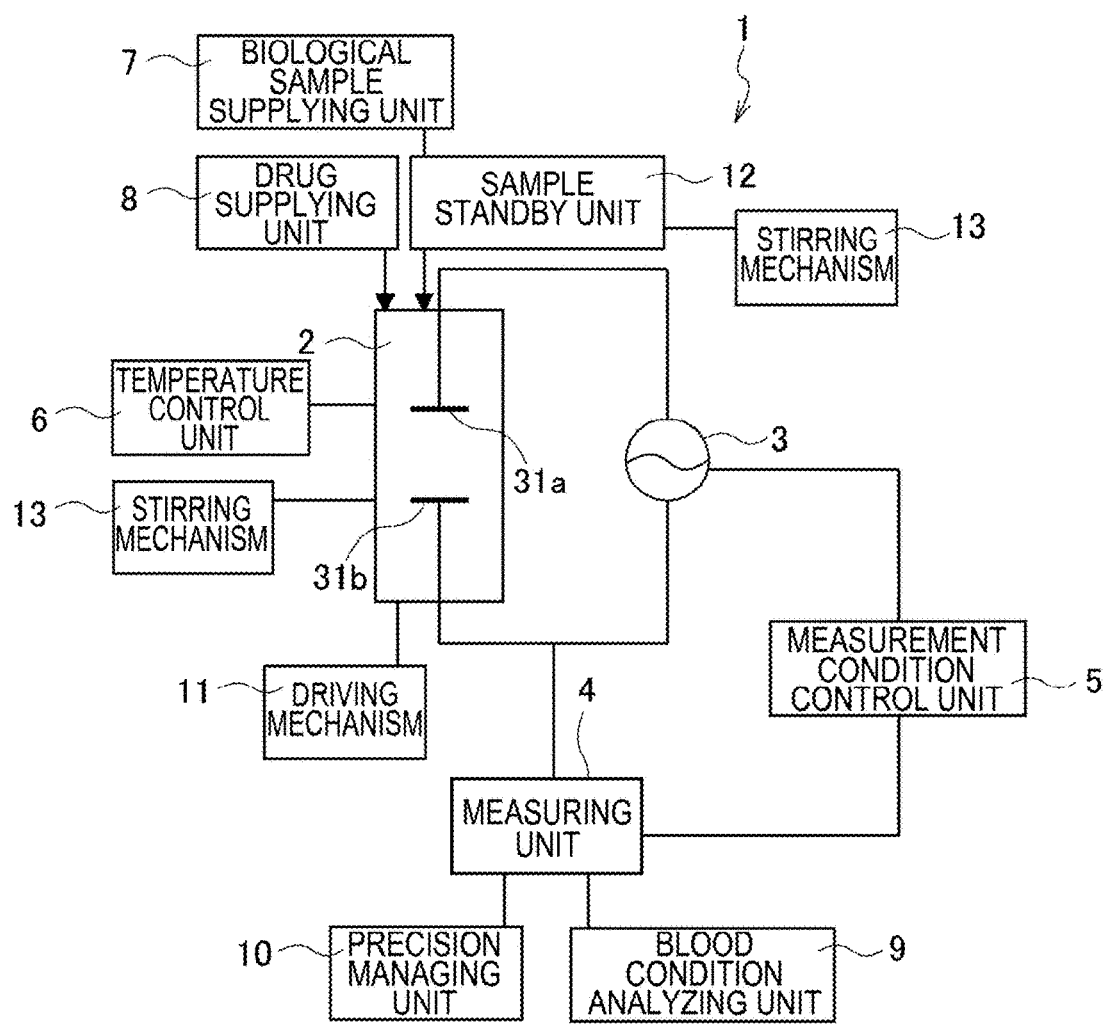
FIG. 1 is a schematic conceptual diagram schematically showing the concept of an impedance measuring device for biological samples 1 according to the present technology.

Hereinbelow, preferred embodiments for carrying out the present technology are described with reference to the drawings. The embodiments described below are examples of the typical embodiments of the present technology, and the scope of the present technology is not construed as being limited by the embodiments. The description is given in the following order:

1. Impedance measuring device for biological samples 1
   (1) Biological sample holding unit 2
   (a) Container 21
   (b) Container holding unit 22
   (2) Applying unit 3
   (a) Electrodes 31a and 31b
   (b) Connection unit 32
   (3) Measuring unit 4
   (4) Measurement condition control unit 5
   (5) Temperature control unit 6
   (6) Biological sample supplying unit 7
   (7) Drug supplying unit 8
   (8) Biological sample S
   (9) Blood condition analyzing unit 9
   (10) Precision managing unit 10
   (11) Driving mechanism 11
   (12) Sample standby unit 12
   (13) Stirring mechanism 13
2. Impedance measuring system for biological samples 100
   (1) Display unit 101
   (2) User interface 102
   (3) Memory unit 103

1. Impedance Measuring Device for Biological Samples 1

FIG. 1 is a schematic conceptual diagram schematically showing the concept of an impedance measuring device for biological samples 1 according to the present technology. The impedance measuring device for biological samples 1 according to the present technology includes, in terms of broad categories, at least a biological sample holding unit 2, an applying unit 3, a measuring unit 4, and a measurement condition control unit 5. The impedance measuring device for biological samples 1 may include, as necessary, a temperature control unit 6, a biological sample supplying unit 7, a drug supplying unit 8, a blood condition analyzing unit 9, a precision managing unit 10, a driving mechanism 11, a sample standby unit 12, a stirring mechanism 13, etc. Each component will now be described in detail.

(1) Biological Sample Holding Unit 2

The biological sample holding unit 2 is a part where a biological sample of the measuring object is held. In the impedance measuring device for biological samples 1 according to the present technology, the number of biological sample holding units 2 is not particularly limited, and one or a plurality of biological sample holding units 2 may be freely disposed in accordance with the amount, type, measurement objective, etc. of the biological sample of the measuring object.

In the impedance measuring device for biological samples 1 according to the present technology, impedance measurement is performed in a state where a biological sample S is held by the biological sample holding unit 2. Hence, the biological sample holding unit 2 is preferably in a configuration capable of being sealed in the state of holding the biological sample S. However, the biological sample holding unit 2 may not be in an airtight configuration to the extent that it is capable of being stationary through the time needed to measure the impedance of the biological sample S and there is no influence on measurement.

Specific methods for introducing the biological sample S into the biological sample holding unit 2 and for making sealing are not particularly limited, and the introduction may be made by an arbitrary method in accordance with the configuration of the biological sample holding unit 2. For example, although not shown in the drawings, a method in which the biological sample holding unit 2 is provided with a lid, and the biological sample S is introduced using a pipette or the like and then the lid is closed to make sealing, a method in which the biological sample holding unit 2 is pierced with a needle from its outer surface, and a biological sample S in a liquid form is injected and then the portion pierced with the needle is sealed with grease or the like to make sealing, etc. are given.

The configuration of the biological sample holding unit 2 is not particularly limited to the extent that the biological sample of the measuring object can be held in the device, and may be designed to be an arbitrary configuration. For example, one or a plurality of cells provided on a substrate may be allowed to function as the biological sample holding unit 2, or one or a plurality of containers may be allowed to function as the biological sample holding unit 2. An aspect of the biological sample holding unit 2 will now be described with reference to FIG. 2.

Figure 2:
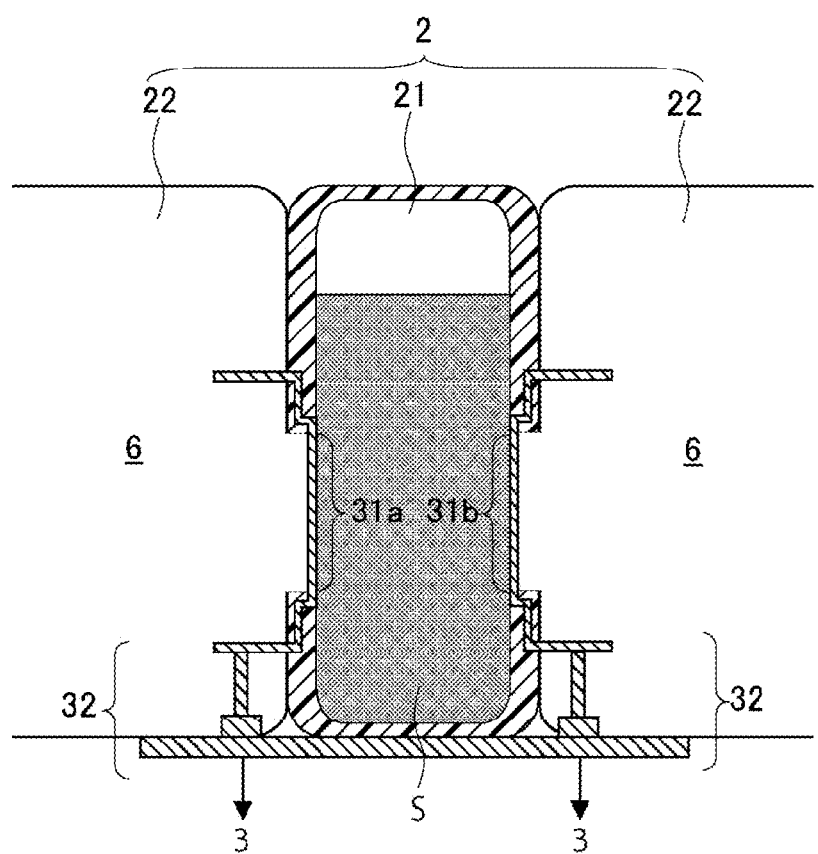
FIG. 2 is a schematic cross-sectional view schematically showing an aspect of a biological sample holding unit 2 in the impedance measuring device for biological samples 1 according to the present technology.

FIG. 2 is a schematic cross-sectional view schematically showing an aspect of the biological sample holding unit 2 in the impedance measuring device for biological samples 1 according to the present technology. The biological sample holding unit 2 illustrated in FIG. 2 is formed of a container 21 and a container holding unit 22.

In the impedance measuring device for biological samples 1 according to the present technology, when the container holding unit 22 is designed so that a known cartridge-type container for measurement can be used as the container 21, the container holding unit 22 by itself can be made to function as the biological sample holding unit 2. That is, the biological sample holding unit 2 in the impedance measuring device for biological samples 1 according to the present technology includes all of the case of being formed of only the container 21, the case of being formed of the container 21 and the container holding unit 22, and the case of being formed of only the container holding unit 22.

(a) Container 21

In the impedance measuring device for biological samples 1 according to the present technology, in the case where the container 21 is used as the biological sample holding unit 2, specific configurations of the container 21 are not particularly limited, and may be freely designed in accordance with the condition, type, etc. of the biological sample S to the extent that the biological sample S of the measuring object can be held, including a circular cylindrical body, a polygonal cylindrical body with a polygonal cross section (triangle, quadrangle, or polygon with more angles), a conical body, a polygonal pyramid-like body with a polygonal cross section (triangle, quadrangle, or polygon with more angles), or a configuration in which one or more of these are combined.

Also the material that forms the container 21 is not particularly limited, and may be freely selected to the extent that there is no influence on the condition, type, measurement objective, etc. of the biological sample S of the measuring object. In the present technology, in particular, the container 21 is preferably formed using a resin from the viewpoint of the ease of processing and molding etc. In the present technology, also the type of usable resin is not particularly limited, and one or more types of resin usable for the holding of the biological sample S may be freely selected for use. For example, a hydrophobic and insulating polymer such as polypropylene, poly(methyl methacrylate), polystyrene, an acrylic, a polysulfone, and polytetrafluoroethylene, a copolymer and a blend polymer thereof, and the like are given. In the present technology, the biological sample holding unit 2 is preferably formed of, among the above materials, particularly one or more types of resin selected from polypropylene, polystyrene, an acrylic, and a polysulfone. These resins have the property of being low coagulation-active against blood, and can therefore be suitably used for the measurement of a biological sample containing blood, for example.

(b) Container Holding Unit 22

In the impedance measuring device for biological samples 1 according to the present technology, in the case where the container holding unit 22 is used as the biological sample holding unit 2, specific configurations of the container holding unit 22 are not particularly limited, and the container holding unit 22 may be freely designed to the extent that the container 21 in which the biological sample S of the measuring object is stored can be held.

Also the material that forms the container holding unit 22 is not particularly limited, and may be freely selected in accordance with the configuration etc. of the container 21 that the container holding unit 22 holds.

(2) Applying Unit 3

The applying unit 3 is a part that applies an AC voltage to a pair of electrodes 31a and 31b that are in contact with the biological sample S held by the biological sample holding unit 2. The applying unit 3 applies a voltage to the pair of electrodes 31a and 31b from, as the starting time point, the time point at which an order to start measurement is received or the time point at which the power supply for the impedance measuring device for biological samples 1 is set to ON. More specifically, the applying unit 3 applies an AC voltage with a set frequency or a frequency controlled in the measurement condition control unit 5 described later to the electrodes 31a and 31b, at set measuring intervals or measuring intervals controlled in the measurement condition control unit 5 described later.

In the applying unit 3, it is also possible to apply an AC voltage to a plurality of pairs of electrodes. As the method for applying an AC voltage to a plurality of pairs of electrodes, for example, a method in which the application of an AC voltage to a plurality of pairs of electrodes is performed simultaneously by a plurality of applying units 3 being provided, a method in which the application of an AC voltage to a plurality of pairs of electrodes is performed by scanning one applying unit 3, a method in which the application of an AC voltage to a plurality of pairs of electrodes is performed by moving the biological sample holding unit 2 including electrodes, a method in which a plurality of applying units 3 are provided and switching is performed to select one or a plurality of applying units 3 that actually perform application, etc. may be given.

(a) Electrodes 31a and 31b

The electrodes 31a and 31b are used to be in contact with the biological sample S at the time of measurement and apply a necessary voltage to the biological sample S. In the impedance measuring device for biological samples 1 according to the present technology, the numbers of electrode units 31a and 31b are not particularly limited to the extent that the impedance of the biological sample S can be measured, and one or more pairs of electrodes may be freely arranged.

Also the arrangement, configuration, etc. of the electrodes 31a and 31b are not particularly limited, and may be freely designed in accordance with the configuration etc. of the biological sample holding unit 2 to the extent that a necessary voltage can be applied to the biological sample S. For example, it is possible, like the biological sample holding unit 2 shown in FIG. 2, to form the electrodes 31a and 31b integrally with the biological sample holding unit 2 (the container 21), or it is possible, although not shown in the drawings, to employ a configuration in which the lid of the container 21 is provided with the electrodes 31a and 31b and sealing is made by the lid to allow the electrodes 31a and 31b to be in contact with the biological sample S stored in the container 21. Furthermore, it is also possible to employ a configuration in which, at the time of measurement, a pair of electrodes 31a and 31b are inserted into the container 21 from the outside of the container 21 to allow the electrodes 31a and 31b to be in contact with the biological sample S.

Also the material that forms the electrodes 31a and 31b is not particularly limited, and one or more types of known electrically conductive material may be freely selected for use to the extent that there is no influence on the condition, type, measurement objective, etc. of the biological sample S of the measuring object. For example, titanium, aluminum, stainless steel, platinum, gold, copper, graphite, and the like are given. In the present technology, the electrodes 31a and 31b are preferably formed of, among the above materials, particularly an electrically conductive material containing titanium. Titanium has the property of being low coagulation-active against blood, and can therefore be suitably used for the measurement of a biological sample containing blood, for example.

(b) Connection Unit 32

A connection unit 32 is a part that electrically connects the applying unit 3 and/or the measuring unit 4 and the electrodes 31a and 31b. Specific configurations of the connection unit 32 are not particularly limited, and the connection unit 32 may be designed in an arbitrary configuration to the extent that the applying unit 3 and/or the measuring unit 4 and the electrodes 31a and 31b can be electrically connected. An aspect of the connection unit 32 will now be described with reference to FIG. 3.

Figure 3:
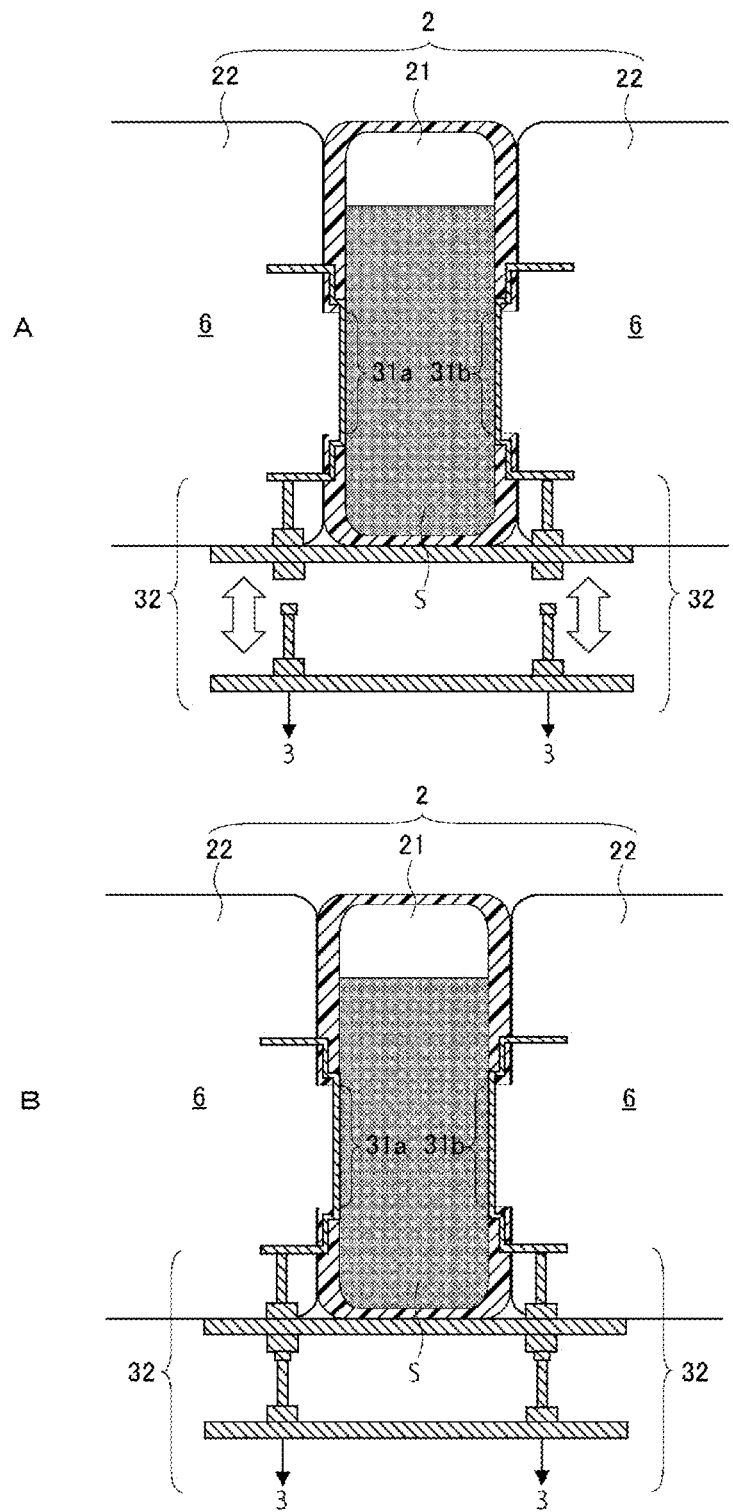
FIG. 3 is a schematic cross-sectional view schematically showing an aspect of a connection unit 32 in the impedance measuring device for biological samples 1 according to the present technology; FIG. A is a schematic cross-sectional view showing a state at the time of non-measurement, and FIG. B is a schematic cross-sectional view showing a state at the time of measurement.

FIG. 3 is a schematic cross-sectional view schematically showing an aspect of the connection unit 32 in the impedance measuring device for biological samples 1 according to the present technology. FIG. 3A shows a state at the time of non-measurement, and FIG. 3B shows a state at the time of measurement. The connection unit 32 illustrated in FIG. 3 is configured so that at the time of non-measurement, the applying unit 3 and/or the measuring unit 4 and the electrodes 31a and 31b are in a non-connection state, and at the time of measurement, the applying unit 3 and/or the measuring unit 4 and the electrodes 31a and 31b can be electrically connected.

Specifically, the container 21 and the connection unit 32 on the container 21 side, the connection unit 32 on the side of the applying unit 3 and/or the measuring unit 4, or all of them are configured to be drivable. At the time of non-measurement, the connection unit 32 on the container 21 side and the connection unit 32 on the side of the applying unit 3 and/or the measuring unit 4 are set to a non-contact state; and at the time of measurement, the connection unit 32 on the container 21 side and the connection unit 32 on the side of the applying unit 3 and/or the measuring unit 4 are driven into a contact state. Thus, the applying unit 3 and/or the measuring unit 4 and the electrodes 31a and 31b can be electrically connected only at the time of measurement.

(3) Measuring Unit 4

The measuring unit 4 is a part that measures the impedance of the biological sample S obtained by an AC voltage being applied to the biological sample S by the applying unit 3. Specifically, the impedance of the biological sample S between the electrodes 31a and 31b is measured from, as the starting time point, the time point at which an order to start measurement is received or the time point at which the power supply for the impedance measuring device for biological samples 1 is set to ON.

A dielectric constant etc. can be derived from the measured impedance. For the derivation of the dielectric constant, a known function or mathematical relation expressing the relationship between the impedance and the dielectric constant may be used.

In the measuring unit 4, the frequency band in which the impedance is measured may be appropriately selected in accordance with the type, condition, measurement objective, etc. of the biological sample to be measured. For example, when the biological sample is blood, a change is seen in the impedance in the frequency bands shown in Table 1 below in accordance with the condition change of the blood.

TABLE 1

| Condition change of blood | Impedance | |
| --- | --- | --- |
| | Frequency at which change is seen | Frequency at which change is more significant |
| Coagulation of blood (blood coagulation) | 1 kHz to 50 MHz | 3 MHz to 15 MHz |
| Fibrin formation | 1 kHz to 50 MHz | 3 MHz to 15 MHz |
| Fibrin clot formation | 1 kHz to 50 MHz | 3 MHz to 15 MHz |
| Blood clot formation | 1 kHz to 50 MHz | 3 MHz to 15 MHz |
| Rouleaux formation of red blood cells | 500 kHz to 25 MHz | 2 MHz to 10 MHz |
| Aggregation of blood | 1 kHz to 50 MHz | 500 kHz to 5 MHz |
| Sedimentation of red blood cells (erythrocyte sedimentation) | 1 kHz to 50 MHz | 100 kHz to 40 MHz |
| Blood clot retraction (retraction) | 1 kHz to 50 MHz | 10 kHz to 100 kHz |
| Hemolysis | 1 kHz to 50 MHz | 3 MHz to 15 MHz |
| Fibrinolysis | 1 kHz to 50 MHz | 3 MHz to 15 MHz |

For example, in the case where the objective is to predict or detect the coagulation of blood (blood coagulation), it is preferable to measure the impedance at frequencies of 1 kHz to 50 MHz, and it is more preferable to measure the impedance at frequencies of 3 MHz to 15 MHz. By setting a parameter in accordance with the condition or measurement objective of blood beforehand in this way, a preferable frequency band like those shown in Table 1 above can be automatically selected.

In the measuring unit 4, it is also possible to perform a plurality of measurements. As the method for performing a plurality of measurements, for example, a method in which a plurality of measurements are performed simultaneously by a plurality of measuring units 4 being provided, a method in which a plurality of measurements are performed by scanning one measuring unit 4, a method in which a plurality of measurements are performed by moving the biological sample holding unit 2, a method in which a plurality of measuring units 4 are provided and switching is performed to select one or a plurality of measuring units 4 that actually perform measurement, etc. may be given.

(4) Measurement Condition Control Unit 5

The measurement condition control unit 5 is a part that controls the measuring time and/or the measuring frequency in the measuring unit 4.

For example, as a specific method for controlling the measuring time, it is possible to control the measuring interval in accordance with the amount of data necessary for the analysis of the objective or the like, or it is possible to control the timing of measurement completion when the measured value has almost leveled off or the like.

It is also possible to control the measuring frequency in accordance with the type of the biological sample S of the measuring object, the measured value necessary for the analysis of the objective, etc. As the control of the measuring frequency, a method in which the frequency of the AC voltage applied between the electrodes 31a and 31b is changed, a method in which a plurality of frequencies are superposed to perform impedance measurement at the plurality of frequencies, etc. are given. As specific methods thereof, a method in which a plurality of single-frequency analyzers are juxtaposed, a method in which the frequency is swept, a method in which frequencies are superposed and the information of each frequency is extracted with a filter, a method in which measurement is performed using the response to an impulse, etc. are given.

(5) Temperature Control Unit 6

The temperature control unit 6 is a part that controls the temperature in the biological sample holding unit 2. In the impedance measuring device for biological samples 1 according to the present technology, although the temperature control unit 6 is not an essential part, it is preferably included in order to keep the biological sample S of the measuring object in an optimum state for measurement.

As described later, in the case where the sample standby unit 12 is provided, the temperature control unit 6 may control the temperature in the sample standby unit 12. In the case where a drug is put in the biological sample S at the time of or before measurement, the temperature control unit 6 may be provided in order to control the temperature of the drug. In this case, the temperature control unit 6 may be provided individually for the temperature control in the biological sample holding unit 2, the temperature control in the sample standby unit 12, and the temperature control of the drug, or one temperature control unit 6 may perform the temperature control of all of them.

Specific temperature control methods are not particularly limited. For example, the container holding unit 22 shown in FIG. 2 and FIG. 3 may be provided with a temperature adjustment function; thereby, the container holding unit 22 can be made to function as the temperature control unit 6.

(6) Biological Sample Supplying Unit 7

The biological sample supplying unit 7 is a part that automatically supplies the biological sample S to the biological sample holding unit 2. In the impedance measuring device for biological samples 1 according to the present technology, although the biological sample supplying unit 7 is not an essential part, it is preferably included in order to perform each process automatically.

Specific methods for supplying the biological sample S are not particularly limited. For example, when the biological sample S is in a liquid form, the biological sample S can be automatically supplied to the biological sample holding unit 2 by using a pipetter and a chip attached to its tip. In this case, the chip is preferably used only once and then thrown away in order to prevent measurement errors etc. It is also possible to automatically supply the biological sample S to the biological sample holding unit 2 from the storage chamber of the biological sample S using a pump or the like. Furthermore, it is also possible to automatically supply the biological sample S to the biological sample holding unit 2 using a permanent nozzle or the like. In this case, the nozzle is preferably provided with a cleaning function in order to prevent measurement errors etc.

(7) Drug Supplying Unit 8

The drug supplying unit 8 is a part that automatically supplies one or more kinds of drug to the biological sample holding unit 2. In the impedance measuring device for biological samples 1 according to the present technology, although the drug supplying unit 8 is not an essential part, it is preferably included in order to perform each process automatically.

Specific methods for supplying a drug are not particularly limited, and a drug may be supplied using similar methods to those for the biological sample supplying unit 7. In particular, the supply of a drug is preferably performed by a method in which a certain amount of a drug can be supplied without contacting the biological sample holding unit 2 (the container 21). For example, a drug in a liquid form may be supplied by discharge.

More specifically, for example, a liquid drug is introduced into a discharge pipe beforehand, and compressed air separately connected via a pipe line connected to the discharge pipe is blown into the pipe line for a short time; thereby, the liquid drug can be discharged and supplied to the biological sample holding unit 2 (the container 21). At this time, the amount of the discharged liquid drug can be adjusted by adjusting the air pressure and the valve opening/closing time.

As well as blowing air, it is also possible to discharge and supply a liquid drug to the biological sample holding unit 2 (the container 21) by utilizing the vaporization of the liquid drug itself or air dissolved therein by heating. At this time, the amount of the discharged liquid drug can be adjusted by adjusting the volume of generated air bubbles by adjusting the voltage applied to a vaporization chamber equipped with a heating element or the like and the time of voltage application.

Furthermore, a liquid drug may be supplied to the biological sample holding unit 2 (the container 21) also by, not using air, driving a movable part provided in a pipe line using a piezoelectric element or the like and sending the liquid drug in the amount determined by the capacity of the movable part.

Furthermore, a drug may be supplied also by, for example, using what is called an inkjet system in which a liquid drug is made into minute droplets and directly sprayed on the designated biological sample holding unit 2 (the container 21).

The drug supplying unit 8 may be provided with a stirring function, a temperature control function, a discrimination function for discriminating the type of the drug or the like (e.g. a bar code reader), etc.

When using a drug, a prescribed drug may be stored in the container 21 beforehand in a solidified form or a liquid form as it is. For example, when a biological sample S containing a blood component or the like is used as the measuring object, an anticoagulant, a coagulation initiator, etc. may be put in the container 21 beforehand.

Thus, by storing a drug in the container 21 beforehand, the drug supplying unit 8 and a drug holding unit become unnecessary, and downsizing of the device and reduction in costs are possible. Furthermore, the time and effort of drug exchange by a user etc. becomes unnecessary, and also the equipment maintenance of the drug supplying unit 8 and the drug holding unit becomes unnecessary; thus, usability can be improved.

(8) Biological Sample S

The biological sample S that can be the measuring object in the present technology is not particularly limited, and may be freely selected. In the impedance measuring device for biological samples 1 according to the present technology, in particular the impedance of a biological sample in a liquid form or a gel form can be suitably measured. Specific examples of the biological sample S in a liquid form include a biological sample S containing a blood component such as whole blood, blood plasma, or a diluted solution and/or a drug-added substance thereof, etc.

(9) Blood Condition Analyzing Unit 9

The blood condition analyzing unit 9 is a part that analyzes the condition change of blood from the temporal change of the impedance measured in the measuring unit 4. In the impedance measuring device for biological samples 1 according to the present technology, the blood condition analyzing unit 9 is not an essential part; but when a biological sample containing a blood component is used as the biological sample S, the condition change of blood can be detected by providing the blood condition analyzing unit 9.

More specifically, for example, the measured values of a plurality of impedances are received during the analysis period, a parameter expressing the feature of each is extracted from the measured values, and the parameter and standard values determining the standards of condition changes of blood are compared; thus, the condition change of blood can be analyzed on the basis of the comparison.

In the blood condition analyzing unit 9 in the present technology, specific examples of the condition change of blood analyzable are not particularly limited to the extent that they are phenomena in which a temporal change in impedance is seen due to a condition change, and various condition changes can be detected and analyzed. For example, the coagulation of blood (blood coagulation), fibrin formation, fibrin clot formation, blood clot formation, blood platelet coagulation, the rouleaux formation of red blood cells, the aggregation of blood, the sedimentation of red blood cells (erythrocyte sedimentation), blood clot retraction, hemolysis such as fibrinolysis, fibrinolysis, etc. may be given.

(10) Precision Managing Unit 10

The precision managing unit 10 is a part that performs the precision management of the measuring unit 4. In the impedance measuring device for biological samples 1 according to the present technology, although the precision managing unit 10 is not an essential part, providing the precision managing unit 10 makes it possible to improve the measurement precision in the measuring unit 4.

Specific methods for managing the precision of the measuring unit 4 performed in the precision managing unit 10 are not particularly limited, and known precision managing methods may be freely selected for use. For example, the method is not limited to methods in which the precision management of the measuring unit 4 is performed by calibrating the measuring unit 4, such as a method in which a metal plate or the like for short-circuiting is installed in the device 1 and before starting measurement the electrodes and the metal plate are short-circuited to calibrate the measuring unit 4, a method in which a jig for calibration or the like and the electrodes are brought into contact, and a method in which a container with an identical configuration to the container 21 for storing a biological sample is equipped with a metal plate or the like and before starting measurement the electrodes and the metal plate are short-circuited to calibrate the measuring unit 4; and precision management may be performed also by using an arbitrary method such as a method in which the precision management of the measuring unit 4 is performed by checking the condition of the measuring unit 4 before actual measurement, and only upon the occurrence of abnormality, calibrating the measuring unit 4 by performing calibration like the above etc.

(11) Driving Mechanism 11

The driving mechanism 11 is used to move the biological sample holding unit 2 in accordance with various purposes. For example, when a biological sample S containing sedimentous components is used as the measuring object, the biological sample holding unit 2 may be moved in a direction that changes the direction of the gravity applied to the biological sample S held by the biological sample holding unit 2; thus, the measured value can be prevented from being influenced by sedimentation of the sedimentous components.

Furthermore, for example like the biological sample holding unit 2 shown in FIG. 3 above, the applying unit 3 and the electrodes 31a and 31b are set to a non-connection state at the time of non-measurement, and at the time of measurement the biological sample holding unit 2 may be driven so that the applying unit 3 and the electrodes 31a and 31b can be electrically connected.

Figure 4:
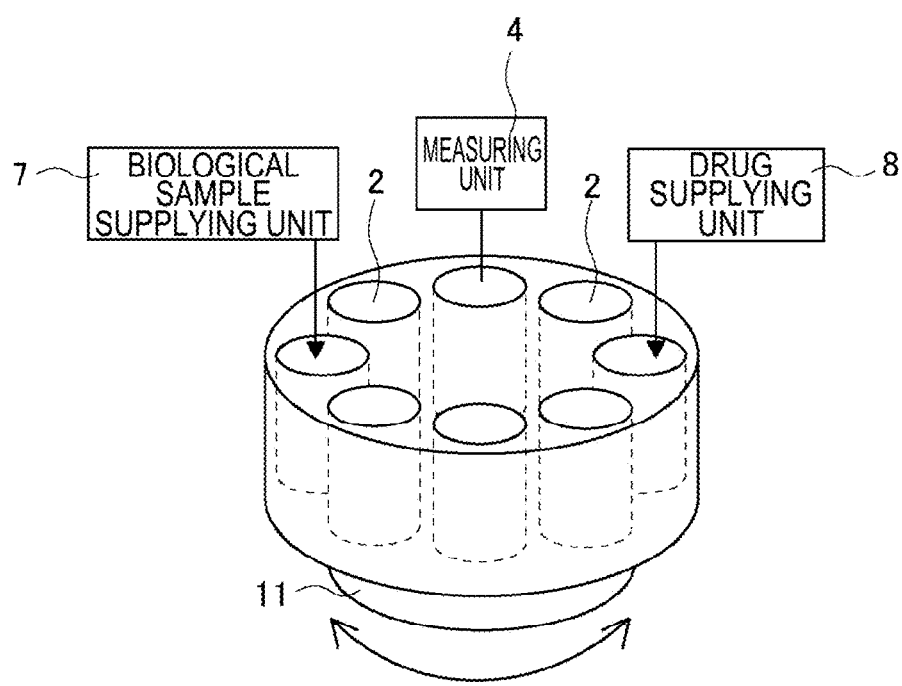
FIG. 4 is a schematic cross-sectional view schematically showing an aspect of a driving mechanism 11 in the impedance measuring device for biological samples 1 according to the present technology.

Furthermore, for example, in the case where a plurality of biological sample holding units 2 are provided, when the biological sample holding unit 2 is configured to be movable like the example shown in FIG. 4, measurement, biological sample supply, drug supply, etc. can be performed by moving the biological sample holding unit 2 to a needed part. That is, since there is no need to move the measuring unit 4, the biological sample supplying unit 7, the drug supplying unit 8, etc. to the biological sample holding unit 2 of the objective, there is no need to provide a driving unit for driving these units etc. and downsizing of the device and reduction in costs are possible.

(12) Sample Standby Unit 12

The sample standby unit 12 is a part that allows aliquoted biological samples S to stand by before measurement. In the impedance measuring device for biological samples 1 according to the present technology, although the sample standby unit 12 is not an essential part, it may be included in order to perform measurement smoothly.

The sample standby unit 12 may be provided with a stirring function, a temperature control function, a mechanism of movement to the biological sample holding unit 2, a discrimination function for discriminating the type of the biological sample S etc. (e.g. a bar code reader etc.), an automatic opening function, etc.

(13) Stirring Mechanism 13

The stirring mechanism 13 is a mechanism that performs stirring in the biological sample holding unit 2. More specifically, the stirring mechanism 13 is a mechanism for stirring the biological sample S itself held in the biological sample holding unit 2 and stirring the biological sample S and a drug such as a reagent. In the impedance measuring device for biological samples 1 according to the present technology, although the stirring mechanism 13 is not an essential part, it is preferably included, for example when sedimentous components are contained in the biological sample S, when a drug such as a reagent is added at the time of measurement, or in other cases. More specifically, for example, when blood is used as the biological sample S, the sedimentation of red blood cells (erythrocyte sedimentation) can be prevented by stirring blood with the stirring mechanism 13.

Specific stirring methods in the stirring mechanism 13 are not particularly limited to the extent that the effect of the present invention is not impaired, and known stirring methods may be freely selected for use. For example, stirring by pipetting, stirring using a stirring rod, a stirring chip, or the like, stirring by inverting a container containing the biological sample S and a drug, etc. may be given.

Figure 5:
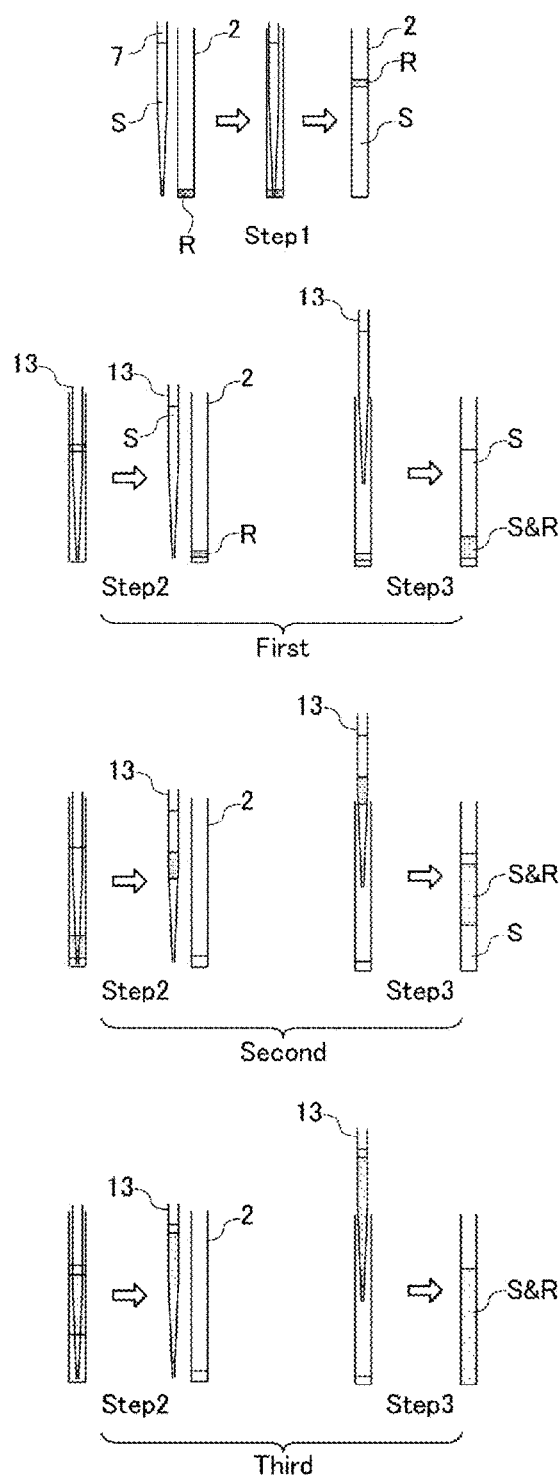
FIG. 5 is a conceptual diagram showing a stirring method when a biological sample S and a reagent R are stirred by pipetting using a stirring mechanism 13.

A specific example of the stirring method will now be described with reference to the drawing. FIG. 5 is a conceptual diagram showing a stirring method in the case where the biological sample S and a reagent R are stirred by pipetting using the stirring mechanism 13.

<Step 1>

In step 1, the biological sample S of the measurement objective is injected beforehand into the biological sample holding unit 2 in which a reagent R is held. To introduce the reagent R into the biological sample holding unit 2, the reagent R may be automatically injected into the biological sample holding unit 2 beforehand using the drug supplying unit 8 described above, or a cartridge in which the reagent R is held beforehand may be used as the biological sample holding unit 2.

The injection of the biological sample S into the biological sample holding unit 2 may be automatically performed by, for example, the biological sample supplying unit 7 described above. Although the biological sample S is discharged in a bottom portion of the biological sample holding unit 2 in the example shown in FIG. 5, the discharge position is not limited to this, and it is also possible to set a parameter in accordance with the type, condition, etc. of the biological sample S beforehand and automatically control the discharge position.

<Step 2>

In step 2, the biological sample S and/or the reagent R is sucked from a prescribed position of the biological sample holding unit 2. Although the suction is performed in a bottom portion of the biological sample holding unit 2 in the example shown in FIG. 5, the suction position is not limited to this, and it is also possible to set a parameter in accordance with the type, condition, etc. of the biological sample S beforehand and automatically control the suction position.

As the pipette used in the pipetting of step 2 and step 3 described later, the pipette used for the injection of the biological sample S in step 1 may be used as it is, or another pipette may be used.

<Step 3>

In step 3, the biological sample S and/or the reagent R sucked in step 2 is discharged from a prescribed position of the biological sample holding unit 2. Although the discharge is performed in a central portion of the biological sample holding unit 2 in the example shown in FIG. 5, the discharge position is not limited to this, and it is also possible to set a parameter in accordance with the type, condition, etc. of the biological sample S beforehand and automatically control the discharge position.

Step 2 and step 3 are taken as one set and pipetting is repeated necessary times; thereby, the biological sample S and the reagent R can be stirred. Although the biological sample S and the reagent R are stirred by repeating step 2 and step 3 for three sets in the example shown in FIG. 5, the number of times of pipetting is not limited to this, and it is also possible to set a parameter in accordance with the types, conditions, amounts, etc. of the biological sample S and the reagent R beforehand and automatically control the number of times of stirring allowable.

2. Impedance Measuring System for Biological Samples 100

Figure 6:
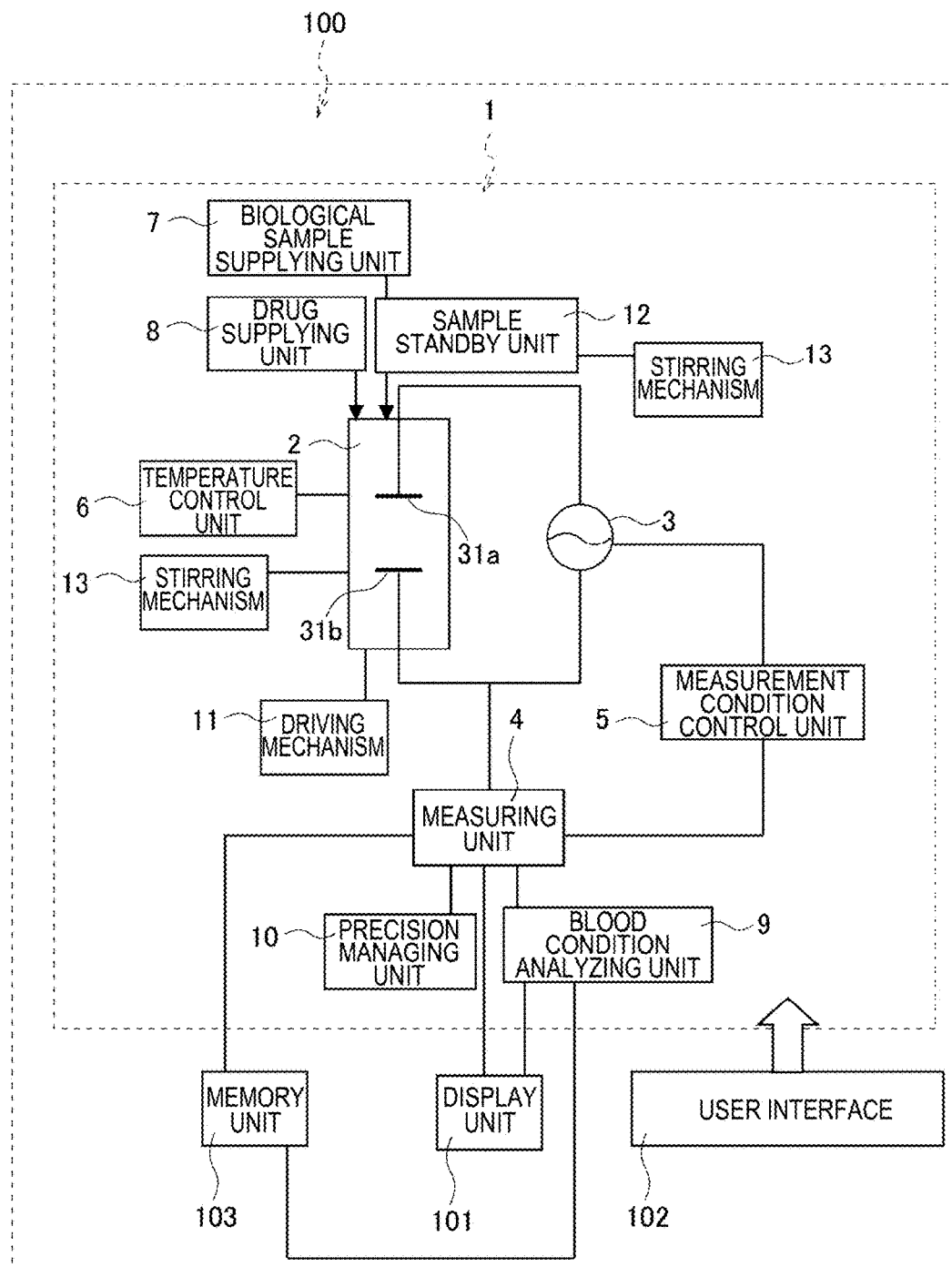
FIG. 6 is a schematic conceptual diagram schematically showing the concept of an impedance measuring system for biological samples 100 according to the present technology.

FIG. 6 is a schematic conceptual diagram schematically showing the concept of an impedance measuring system for biological samples 100 according to the present technology. The impedance measuring system for biological samples 100 according to the present technology includes, in terms of broad categories, at least the biological sample holding unit 2, the applying unit 3, the measuring unit 4, the measurement condition control unit 5, a display unit 101, and a user interface 102. The impedance measuring system for biological samples 100 may include, as necessary, the temperature control unit 6, the biological sample supplying unit 7, the drug supplying unit 8, the blood condition analyzing unit 9, the precision managing unit 10, the driving mechanism 11, a memory unit 103, etc. Each component will now be described in detail. The biological sample holding unit 2, the applying unit 3, the measuring unit 4, the measurement condition control unit 5, the temperature control unit 6, the biological sample supplying unit 7, the drug supplying unit 8, the blood condition analyzing unit 9, the precision managing unit 10, and the driving mechanism 11 are the same as those of the impedance measuring device for biological samples 1 described above, and a description is omitted herein.

(1) Display Unit 101

Figure 7:
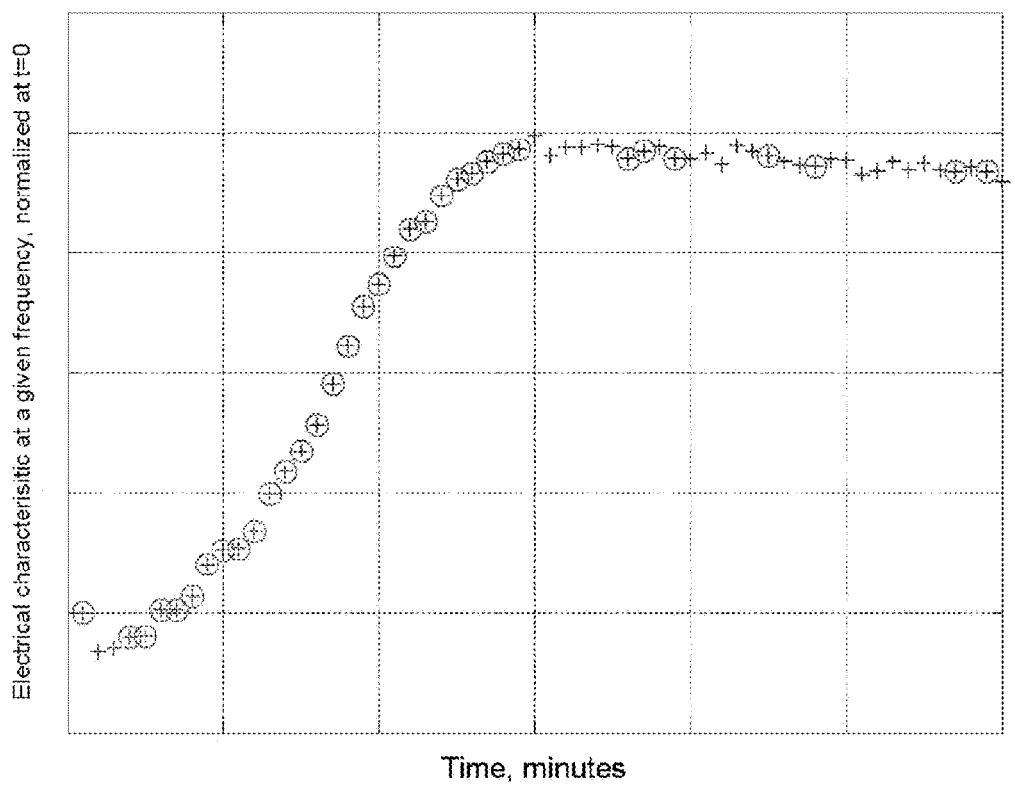
FIG. 7 is a drawing-substitute graph showing an example of data displayed on a display unit in the impedance measuring system for biological samples 100 according to the present technology.

The display unit 101 is a part that displays the data of the impedance measured in the measuring unit 4. The display unit 101 may display the numerical data of the impedance measured in the measuring unit 4 as they are, or may display a graph of the data, for example. FIG. 7 shows an example of data displayed on the display unit 101.

It is also possible to use the data of the impedance measured in the measuring unit 4 to analyze the properties etc. of the biological sample S and display the analyzed data.

(2) User Interface 102

The user interface 102 is a part for a user's operation. A user can access each part of the impedance measuring device for biological samples 1 according to the present technology through the user interface 102.

(3) Memory Unit 103

The memory unit 103 is a part that stores the data of the impedance measured in the measuring unit 4. The memory unit 103 may store the data of the impedance measured in the measuring unit 4 as they are, or may store analyzed data obtained by analyzing the properties etc. of the biological sample S using the data of the impedance measured in the measuring unit 4.

In the impedance measuring system for biological samples 100 according to the present technology described above, the impedance measuring device for biological samples 1, the display unit 101, the user interface 102, and the memory unit 103 may be connected to each other via a network.

Additionally, the present technology may also be configured as below.

(1)
An impedance measuring device for biological samples including:
one or a plurality of biological sample holding units configured to hold a biological sample;
an applying unit configured to apply an AC voltage to a pair of electrodes in contact with the biological sample held by the biological sample holding unit;
a measuring unit configured to measure an impedance of the biological sample obtained by an AC voltage being applied to the biological sample by the applying unit; and
a measurement condition control unit configured to control a measuring time and/or a measuring frequency in the measuring unit.

(2)
The impedance measuring device for biological samples according to (1), wherein in control of the measuring time in the measurement condition control unit, a measuring interval in the measuring unit is controlled.

(3)
The impedance measuring device for biological samples according to (1) or (2), wherein in control of the measuring time in the measurement condition control unit, a timing of measurement completion in the measuring unit is controlled.

(4)
The impedance measuring device for biological samples according to any one of (1) to (3), further including:
a temperature control unit configured to control a temperature in the biological sample holding unit.

(5)
The impedance measuring device for biological samples according to any one of (1) to (4), wherein in the biological sample holding unit, a biological sample is held by holding a container in which the biological sample is stored.

(6)
The impedance measuring device for biological samples according to (5), further including:
a biological sample supplying unit configured to supply the biological sample to the biological sample holding unit automatically.

(7)
The impedance measuring device for biological samples according to (5) or (6), further including:
a drug supplying unit configured to supply one or more kinds of drug to the biological sample holding unit automatically.

(8)
The impedance measuring device for biological samples according to (5) or (6), wherein one or more kinds of drug are stored in the container beforehand.

(9)
The impedance measuring device for biological samples according to any one of (1) to (8), wherein the biological sample contains a blood component.

(10)
The impedance measuring device for biological samples according to (9), further including:
a blood condition analyzing unit configured to analyze a condition change of blood from a temporal change of an impedance measured in the measuring unit.

(11)
The impedance measuring device for biological samples according to any one of (1) to (10), further including:
a precision managing unit configured to perform management of precision of the measuring unit.

(12)
The impedance measuring device for biological samples according to any one of (1) to (11), further including:
a driving mechanism configured to move the biological sample holding unit.

(13)
The impedance measuring device for biological samples according to (12), wherein the driving mechanism moves the biological sample holding unit in a direction that changes a direction of gravity applied to the biological sample held by the biological sample holding unit.

(14)
The impedance measuring device for biological samples according to any one of (1) to (12), further including:
a stirring mechanism configured to perform stirring in the biological sample holding unit.

(15)
An impedance measuring system for biological samples including:
one or a plurality of biological sample holding units configured to hold a biological sample;
an applying unit configured to apply an AC voltage to a pair of electrodes in contact with the biological sample held by the biological sample holding unit;
a measuring unit configured to measure an impedance of the biological sample obtained by an AC voltage being applied to the biological sample by the applying unit;
a measurement condition control unit configured to control a measuring time and/or a measuring frequency in the measuring unit;
a display unit configured to display data of an impedance measured in the measuring unit; and
a user interface for a user's operation.

(16)
The impedance measuring system for biological samples according to (15), further including:
a memory unit configured to store data of an impedance measured in the measuring unit.

INDUSTRIAL APPLICABILITY

The impedance measuring device and system for biological samples according to the present technology can automatically control the measuring time and/or the measuring frequency, and can therefore, in the impedance measurement of a biological sample, improve measurement precision rapidly in accordance with the type, analysis objective, etc. of the biological sample.

REFERENCE SIGNS LIST 1 impedance measuring device for biological samples
2 biological sample holding unit
21 container
22 container holding unit
3 applying unit
31a, 31b electrode
32 connection unit
4 measuring unit
5 measurement condition control unit
6 temperature control unit
7 biological sample supplying unit
8 drug supplying unit
9 blood condition analyzing unit
10 precision managing unit
11 driving mechanism
12 sample standby unit 13 stirring mechanism
100 impedance measuring system for biological samples
101 display unit
102 user interface
103 memory unit
R reagent
S biological sample

The invention claimed is:

1. A method of operating an impedance measuring device for biological samples comprising:
    applying an AC voltage to a pair of electrodes connected to a biological sample holding unit;
    measuring an impedance of a biological sample by applying an AC voltage to the pair of electrodes;
    controlling a measuring time and/or a measuring frequency when applying the AC voltage; and
    calibrating the impedance measuring device based on an electrical connection between the pair of electrodes.

2. The method according to claim 1, wherein in control of the measuring time, a measuring interval is controlled.

3. The method according to claim 1, wherein in control of the measuring time, a timing of measurement completion is controlled.

4. The method according to claim 1, further comprising controlling a temperature in the biological sample holding unit.

5. The method according to claim 1, wherein in the biological sample holding unit, the biological sample is held by holding a container in which the biological sample is stored.

6. The method according to claim 1, further comprising supplying, by a biological sample supplying unit, the biological sample to the biological sample holding unit automatically.

7. The method according to claim 1, further comprising supplying, by a drug supplying unit, one or more kinds of drugs to the biological sample holding unit automatically.

8. The method according to claim 5, wherein one or more kinds of drug are stored in the container beforehand.

9. The method according to claim 1, wherein the biological sample contains a blood component.

10. The method according to claim 9, further comprising analyzing a condition change of blood from a temporal change of the measured impedance.

11. The method according to claim 1, wherein the calibrating of the impedance measuring device is executed in response to detecting an abnormality of the impedance measuring device.

12. The method according to claim 1, further comprising moving, by a driving mechanism, the biological sample holding unit.

13. The method according to claim 12, wherein the driving mechanism moves the biological sample holding unit in a direction that changes a direction of gravity applied to the biological sample held by the biological sample holding unit.

14. The method according to claim 1, further comprising stirring the biological sample by a stirring mechanism that is configured to perform stirring in the biological sample holding unit.

15. A method of measuring impedance for biological samples with an impedance measuring system, the method comprising:
    holding one or a plurality of biological samples in one or a plurality of biological sample holding units;
    applying an AC voltage to a pair of electrodes in contact with a first biological sample held by a first biological sample holding unit of the one or a plurality of biological sample holding units;
    measuring an impedance of the first biological sample based on the AC voltage applied to the pair of electrodes;
    controlling a measuring time and/or a measuring frequency when applying the AC voltage;
    calibrating the impedance measuring system based on an electrical connection between the pair of electrodes;
    displaying impedance data that is representative of an impedance measured based on the applied AC voltage; and
    displaying a user interface for a user's operation.

16. The method according to claim 15, further comprising storing, in a memory unit, at least some of the impedance data.

* * * * *